(12) United States Patent
Vilanova et al.

(10) Patent No.: US 7,356,420 B2
(45) Date of Patent: Apr. 8, 2008

(54) ANALYZING SYSTEM FOR THE DETECTION OF REDUCING AND OXIDIZING GASES IN A CARRIER GAS WITH A METAL-OXIDE-SEMICONDUCTOR SENSOR ARRANGEMENT

(75) Inventors: Xavier Vilanova, Tarragona (ES); Xavier Correig, Tarragona (ES); Eduard Llobet, Tarragona (ES); Jesús Brezmes, Tarragona (ES); Raul Calavia, Tarragona (ES); Xavier Sanchez, Bellaterra (ES)

(73) Assignee: Sociedad Epanola De Carburos Metalicas, S.A., Bellaterra (ES)

( * ) Notice: Subject to any disclaimer, the term of this patent is extended or adjusted under 35 U.S.C. 154(b) by 0 days.

(21) Appl. No.: 10/538,585

(22) PCT Filed: Dec. 23, 2003

(86) PCT No.: PCT/IB03/06442

§ 371 (c)(1),
(2), (4) Date: Jun. 15, 2005

(87) PCT Pub. No.: WO2004/061445

PCT Pub. Date: Jul. 22, 2004

(65) Prior Publication Data

US 2006/0052953 A1 Mar. 9, 2006

(30) Foreign Application Priority Data

Jan. 2, 2003 (ES) .................. 200300003

(51) Int. Cl.
*G01N 31/00* (2006.01)
(52) U.S. Cl. ..................................... 702/22
(58) Field of Classification Search .................. 702/24, 702/22; 73/31.06; 340/634
See application file for complete search history.

(56) References Cited

U.S. PATENT DOCUMENTS 4,423,407 A * 12/1983 Zuckerman .................. 338/34

(Continued)

FOREIGN PATENT DOCUMENTS

DE 19534557 3/1997

OTHER PUBLICATIONS

Llobel, Brezmes, Vilanova, Fondevila, Correig; "Quantitative vapor analysis using the transient response of non-selective thick-film tin oxide gas sensors;" Jun. 16-19, 1997; Solid State Sensors and Actuators, 1997; TRANSDUCERS '97 Chigaco.; 1997 International Converene on Solid-State Sensors and Actuators; pp. 971-974.*

(Continued)

*Primary Examiner*—John Barlow
*Assistant Examiner*—Lisa Sievers
(74) *Attorney, Agent, or Firm*—Wolf Block Schorr & Solis-Cohen LLP

(57) ABSTRACT

Analyzing system for the detection of reducing and oxidizing gases in a carrier gas, wherein the detection means are sensors based on semiconductor-type metal oxides that work in the absence of oxygen. The system includes means for connecting to a chamber which contains the sensors, and moreover in that the processing and control include a system of real-time recognition of the gases, which provides a diagram in which the measurements taken on the carrier gas are situated and identified. The analyzing system permits analysis of the gas in real time.

13 Claims, 4 Drawing Sheets

U.S. PATENT DOCUMENTS

| | | | |
|---|---|---|---|
| 5,469,369 A | * | 11/1995 | Rose-Pehrsson et al. ..... 702/27 |
| 5,959,191 A | * | 9/1999 | Lewis et al. ............... 73/31.05 |
| 6,122,954 A | | 9/2000 | Bowers ...................... 73/24.06 |
| 6,484,563 B1 | * | 11/2002 | Enquist et al. ............. 73/31.06 |
| 6,679,097 B2 | * | 1/2004 | Kurokawa et al. ........... 73/19.1 |

OTHER PUBLICATIONS

Visser, Soltis, Rimai, Logothetis; "Sensors for measuring combustibles in the absence of oxygen;" Jun. 24-27, 1991;Solid-State Sensors and Actuators, 1991; Digest of Technical Papers, TRANSDUCERS '91; 1991 International Conference on Solid-State Sensors and Actuators; pp. 555-557.*

Wilson, D., Hoyt, S., Janata, J., Booksh, K. Obando, L.; "Chemical Sensors for Portable, Handheld Field Instruments," Dec. 2001, IEEE Sensors Journal, vol. 1, No. 4, pp. 259-263.*

Hoefer et al. "CO and $CO_2$ Thin-Film $SnO_2$ Gas Sensors on Si Substrates". Sensors and Actuators B, Elsevier Sequoia S.A., Lausanne, CH, vol. 22, No. 2, Nov. 1, 1994, pp. 115-119, XP004012434 ISSN: 0925-4005.

Kim et al. "$CO_2$ -Sensing Characteristics of $SnO_2$Thick Film by Coating Lanthanum Oxide". Sensors and Actuators B, Elsevier Sequoia S.A. Lausanne, CH, vol. 62, No. 1, Jan. 2000, pp. 61-66, XP004184491 ISSN: 0925-4005.

Llobet et al. "Quantitative Vapor Analysis Using the Transient Response of Non-Selective Thick-Film Tin Oxide Gas Sensors". 1997 International Conference on Solid-State Sensors and Actuators. Digest of Technical Papers. Transducers 97. Chicago, IL, Jun. 16-19, 1997. Sessions 3A1-4D3. Papers No. 3A1.01-4D3.14P, International Conference on Solid-State Sensors and Actu, vol. 2, Jun. 16, 1997, pp. 971-974, XP010240638 ISBN: 0-7803-3829-4.

* cited by examiner

ANALYZING SYSTEM FOR THE DETECTION OF REDUCING AND OXIDIZING GASES IN A CARRIER GAS WITH A METAL-OXIDE-SEMICONDUCTOR SENSOR ARRANGEMENT

This invention relates to an analyzing system for the detection of reducing and oxidizing gases and the real-time control of the quality of a carrier gas flow. It also relates to the utilization, in the absence of oxygen, of gas sensors based on semiconductor-type metal oxides.

BACKGROUND OF THE INVENTION

The most usual technique for assessing the quality of a carrier gas, such as carbon dioxide, involves the use of specific chromatography equipment, which include various types of detectors to ensure the sensitivity and selectivity of analysis of the habitual contaminants present in carbon dioxide. In addition to being expensive, such equipment has the disadvantage of not permitting continuous monitoring of the gas being used in production. Such pieces of equipment only carry out ad hoc sample analysis. This technique is used habitually in production centers to evaluate the quality of the dioxide obtained, but as such equipment is expensive it can hardly be installed in any plant that consumes carbon dioxide, such as a carbonated drinks bottling plant. One alternative is to take ad hoc samples that can be sent to the pertinent laboratory for analysis. However, this system does not permit continuous monitoring of the gas flow, while the costs involved therein are far from negligible.

Known in the market are analyzing systems for analyzing the quality of carbon dioxide, comprising various types of specialized equipment such as:

- sulfur compounds analyzers, generally based on pyro-luminiscence systems;
- aromatic hydrocarbon analyzers, based on PID (Photo Ionization Detector) systems with ultraviolet-light lamp;
- total hydrocarbons analyzers, based on FID (Flame Ionization Detector) systems.

Such analysis systems have the disadvantage of being expensive for installing in carbon dioxide consuming plants, while neither do they permit the carrying out of a real-time analysis of a continuous flow of carbon dioxide.

There exists in the market no low-cost system capable of carrying out an (even partial) real-time analysis of the quality of carbon dioxide.

None of the habitual techniques used for evaluating the quality of carbon dioxide is based on the utilization of sensors based on semiconductor-type metal oxides.

Known in the art are gas sensors based on semiconductor-type metal oxides for the detection of gases such as toxic gases in the atmosphere. These are simple, low-cost and robust sensors.

Sensors based on semiconductor-type metal oxides have been developed for the detection of reducing and oxidizing gases in the presence of pure air and, therefore, in the presence of oxygen.

It is known that in the presence of pure air the active material or semiconductor metal oxide (type n), when heated to a temperature between 300° C. and 500° C., adsorbs atmospheric oxygen until it reaches a state of equilibrium. The process of adsorption of an oxygen atom involves the taking up of an electron from the conduction band of the metal oxide. Therefore, when a sensor is in the presence of pure air and in equilibrium, it shows high electrical resistance, also called base resistance.

It is known that if the sensor is exposed to the presence of a reducing gas, the gas will react with the adsorbed oxygen, once again establishing a state of equilibrium. In this case, the concentration of adsorbed oxygen atoms will be lower than that which existed in the presence of pure air, and this will show itself in a larger number of electrons on the conduction band. This results in a very marked reduction of sensor resistance. This effect is reversible, for the sensor can recover its base resistance if it is once again exposed to the presence of pure air.

In the presence of an oxidizing gas, competition arises around the adsorption sites between that gas and the oxygen. This shows itself in new state of equilibrium in which the sensor resistance increases. This effect is in turn reversible.

It is known that the operational principle of the type of sensors described can be summarized in that the conductance of such devices changes progressively with the changes that take place in the composition of the atmosphere.

No sensors are known, however, based on semiconductor-type metal oxides that permit the detection of reducing and oxidizing gases in the complete absence of oxygen in a carrier gas atmosphere or current.

DESCRIPTION OF THE INVENTION

The objective of this invention is to solve the disadvantages mentioned by developing an analyzing system for the detection of reducing and oxidizing gases in a carrier gas which evaluates the quality of the carrier gas in real time, by using gas sensors based on semiconductor-type metal oxides that work in the absence of oxygen.

In accordance with this objective, the analyzing system of this invention comprises a plurality of detecting means, calibrating means, means for processing and control of acquisition and data recognition, and is characterized in that said gas-detection means are sensors based on semiconductor-type metal oxides that work in the absence of oxygen, in that said system includes means for connecting said carrier gas to a measuring chamber which contains said sensors, and in that said means of processing and control include a system of real-time recognition of said gases, which provides a diagram with delimited decision zones, in which the measurements taken on said carrier gas are situated and identified.

Thanks to its characteristics, the analyzing system permits the carrying out of real-time analysis of the quality of a carrier gas, such as carbon dioxide. This is low-cost equipment that can be applied in plants that consume gases, such as carbon dioxide, as in carbonated drinks bottling plants.

In accordance with the invention, the system is characterized in that said calibration means include a plurality of patterns or calibrated gases at least equal in number to the number of reducing and oxidizing gases that have to be detected in the carrier gas, and in that the response of the plurality of sensors to the measurements of said patterns includes the obtaining of a vector of conductance variation for each calibrated gas or standard.

In accordance with the invention, said recognition system comprises obtaining a learning matrix resulting from grouping the conductance variation vectors of the measurements taken with the plurality of patterns or calibrated gases.

In accordance with the objective of this invention, said recognition system identifies the measurements taken in the carrier gas, according to the algorithm:

obtaining a vector of conductance variation for the plurality of sensors that make up the system.

auto scaling of the vector with the mean values and variances used to auto scale the learning matrix obtained from the patterns or calibrated gases.

projecting the auto scaled vector onto the space of the principal components extracted on the basis of the learning matrix obtained with the calibration means.

depending on the position occupied by said vector, the system identifies a type of response.

Preferably, the type of response identified by the system includes the responses of pure carrier gas, contaminated carrier gas at alert level due to at least one contaminant and contaminated carrier gas at alarm level due to at least one contaminant.

Advantageously, the system is characterized in that said processing and control means include a microprocessor that corrects temporary deviations of the sensor responses and controls and processes the data that permit detection of the presence of reducing and/or oxidizing gases at various pre-established levels.

Preferably, said connecting means comprise a plurality of electrically operated valves and connecting pipes to permit the carrier gas or calibrated gases to flow through the chamber that contains the sensors.

According to a preferred embodiment of the invention, the carrier gas is carbon dioxide.

In accordance with the invention, the utilization of a gas sensor based on semiconductor-type metal oxides is proposed for detecting reducing and oxidizing gases present in a carrier gas, in the absence of oxygen.

Absence of oxygen in the carrier gas refers here to oxygen values in said gas not exceeding 30 ppm of oxygen.

BRIEF DESCRIPTION OF THE DRAWINGS

For a better understanding of the matters described, some drawings are attached which, schematically and solely by way of non-restrictive example, show a practical case of embodiment.

In said drawings.

DESCRIPTION OF A PREFERRED EMBODIMENT

Figure 1A:
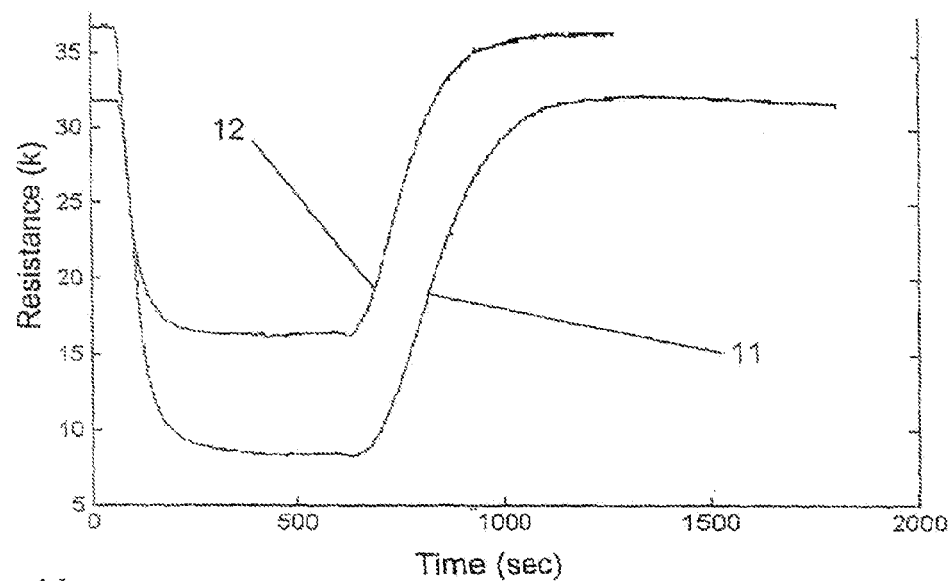
FIG. 1 shows the response of two sensors based on tin oxide to 15 ppm of methane diluted in carbon dioxide (FIG. 1a) and 1 ppm of sulfur dioxide diluted in carbon dioxide (FIG. 1b).
Figure 1B:
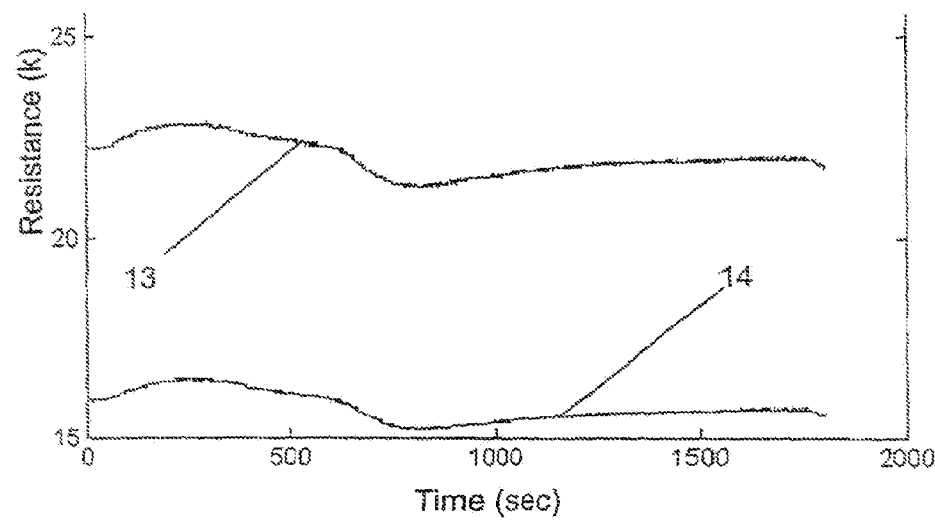

FIGS. 1a and 1b show the response of two gas sensors based on tin dioxide (type-n semiconductor) to the presence of traces of methane and of sulfur dioxide, respectively, diluted in carbon dioxide.

The gas sensors based on semiconductor-type metal oxides of this invention detect oxidizing and reducing gases in a continuous current of carbon dioxide, in the absence of oxygen, that is, at an oxygen concentration in the carbon dioxide at levels not exceeding 30 ppm of oxygen.

FIG. 1a of this invention shows the response 1 of a sensor based on tin oxide (type-n semiconductor) to 15 ppm of methane diluted in carbon dioxide, together with the base resistance 2 of the same sensor when in a state of equilibrium with the carbon dioxide. The presence of the reducing gas leads to a decrease of sensor 2 resistance. This effect is reversible, since the sensor can recover its base resistance 2 if the reducing gas, in this case methane, is eliminated and the sensor once again exposed to the carbon dioxide. FIG. 1b of this invention shows the response 3 of another sensor based on tin oxide (type-n semiconductor) to 1 ppm of sulfur dioxide diluted in carbon dioxide, together with the base resistance 4 of the same sensor when in a state of equilibrium with the carbon dioxide. In this case, the presence of an oxidizing gas leads to an increase in the resistance 4 of the sensor. This effect is again reversible.

It has been observed that carbon dioxide interacts reversibly with the surface of the metal oxide, acting in a similar way to oxygen in the detection of traces of contaminants (reducing and oxidizing gases).

Gas sensors in general, and sensors based on metal oxides in particular, are not very selective. This means that all the sensors show different, though not nil, responses to the contaminant gases. It is therefore necessary to use an array of several sensors based on metal oxides, with partially overlapping sensitivities, in order to be able to identify the various contaminant gases in the carbon dioxide.

Figure 2:
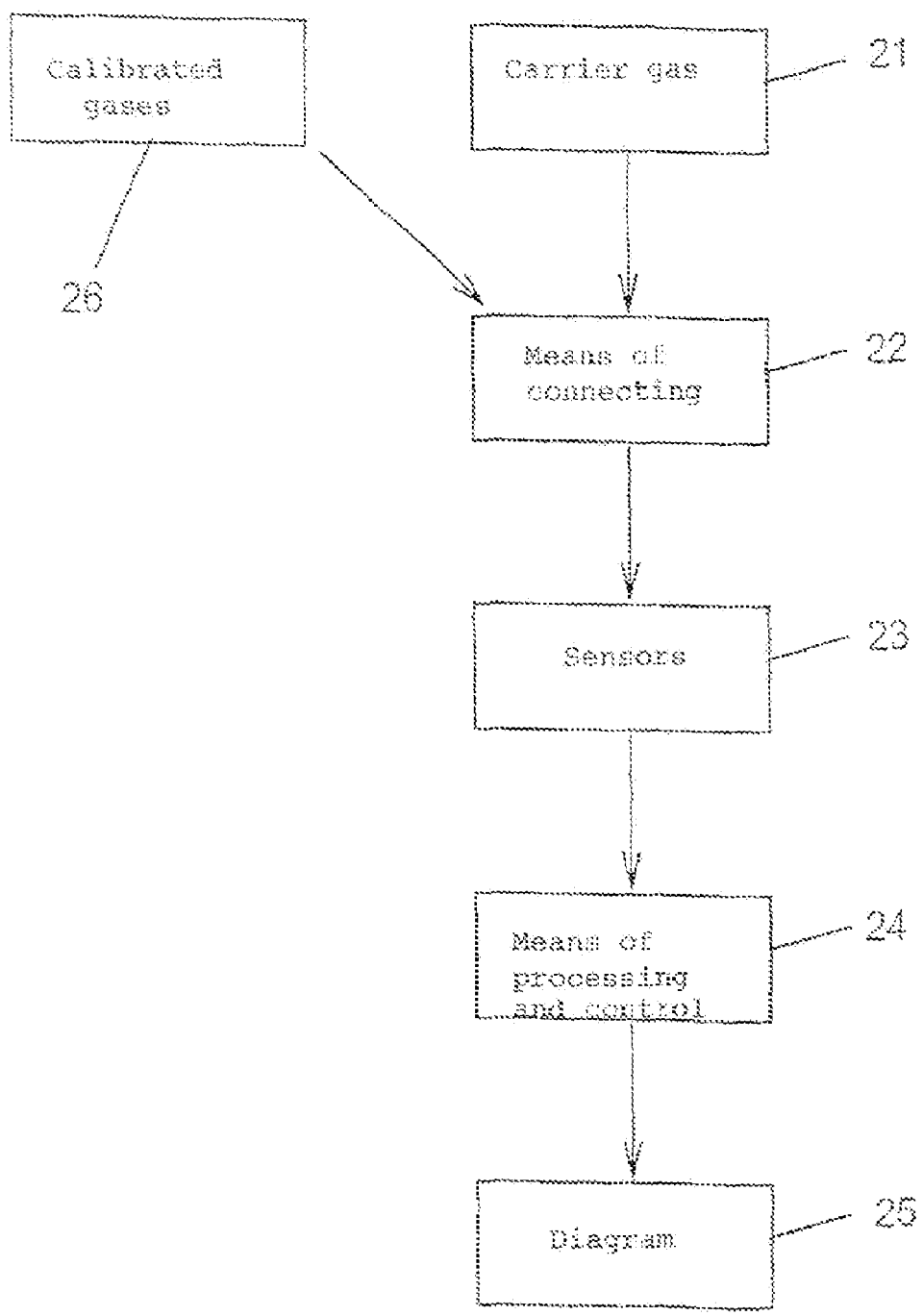
FIG. 2 shows a block diagram of operation of the analyzing system.

FIG. 2 of this invention shows a block diagram that facilitates understanding of the functioning of the analyzing system. Said system consists in a measuring chamber, made of stainless steel, which contains seven sensors 23 based on metal oxides, provided with different catalytically active noble metals. The number of sensors bears a relationship with the number of contaminant gases that must be detected in the carrier gas 21 or carbon dioxide whose quality is to be evaluated. In the example in question, the sensors were chosen for detecting gases such as methane, propane, butane, hexane and other organic compounds, such as ethylene. The system includes means of connecting 22 the carbon dioxide 21 to the measuring chamber, which contains the sensors 23. These consist in a variable number of electrically operated valves, made of stainless steel, to permit the gas whose quality is to be evaluated, or else different calibrated gases 26 or calibration patterns, to flow through the chamber in which the sensors 23 are located. The flow of the gases must be set to a constant value, preferably 100 ml/min.

The resistance reading of the sensors is implemented by means of a semi-bridge of resistances, in which one resistance is the sensor (Rs) itself and the other is a fixed resistance (Rm) of appropriate value. A known voltage (Vc) is applied to both resistances connected in series and the voltage is measured at the intermediate point (Vm). This voltage is converted from analog voltage to digital voltage by an analog-digital converter A/D.

The sensors are heated by means of electronic circuits which permit the sensors to be heated up to their optimum operational temperature (between 300 and 400° C.).

A program implemented by a microprocessor 24 carries out the following functions:

a) Control of the electrically operated valves during both the normal measuring phase and the equipment calibration phase.

b) Control of the process of taking up the Vm voltages and their A/D conversion.

c) Obtaining the voltage Vm for each sensor in the bank, once each second, and calculating the average of the Vm values over the course of one minute. For each sensor, therefore, the average Vm values are from then on calculated on the basis of the last sixty measurements taken.

d) Obtaining the resistances for each one of the sensors in the bank, using the average of the Vm values. Thus, with the average $Vm_i$ value known, the resistance $R_i$ for the i-nth sensor in the bank is obtained by means of the calculation:

$$R_i = VcR_m/(Vc-Vm_i)$$

e) Calculating the conductance values, once the resistance values of the sensors have been calculated. The conductance value variation $\Delta G_i$ for the i-nth sensor is defined by means of the expression: $\Delta G_i = 1/R_i - 1/R_{oi}$, where $R_{oi}$ is the resistance of the sensor in the presence of the pure gas analyzed, or base resistance of the i-nth sensor.

f) Obtaining the vector of conductance variation for each measurement; vector $I = (\Delta G_i, \ldots, \Delta G_n)$, where n is the number of sensors making up the bank. Said vector constitutes the starting information for a recognition algorithm, which then evaluates the quality of the gas being analyzed.

g) Periodic downloading of the information generated by the analyzing system to an Internet address. If levels of any contaminant above preset values are detected, the system can send alert and/or alarm messages to mobile telephones.

The analyzing system described includes a data-recognition system 24 based on a learning process that takes measurements using a set of patterns or calibrated gases 26. The response of the recognition 24 system will be one of the following three: a) Pure carbon dioxide identified. b) Contaminated carbon dioxide at alert-level concentration identified. The contaminant(s) is(are) as follows: list of contaminants. c) Contaminated carbon dioxide at alarm-level concentration identified. The contaminant(s) is(are) as follows: list of contaminants.

The learning process consists in taking measurements using a set of patterns or calibrated gases 26. The patterns consist in pure carbon dioxide and contaminated carbon dioxide. Two calibrated patterns are used for each contaminant considered: one standard with the contaminant diluted to the alert concentration of carbon dioxide and the other diluted to the alarm concentration. Finally, patterns with binary mixtures of contaminants are also used. Each measurement is repeated at least three times in order to achieve a representative set of measurements. This learning process makes it possible to achieve a learning matrix, A, resulting from grouping together the conductance variation vectors obtained in response to the learning measurements described above. The dimension of A is mxn, where m (rows) is the number of learning measurements and n (columns) is the number of sensors forming part of the bank. Thus, each of the rows of A corresponds to one of the learning measurements, and each of the columns of A contains the conductance variations undergone by one sensor of the bank.

The matrix A is standardized by means of an auto scaling operation. This operation is carried out by columns. The mean and the standard deviation of each column are obtained. If $M_i$ and $D_i$ are, respectively, the mean and the standard deviation of column i, then the new value of any element of that column is calculated as a new by means of $e_{ki} = (e_{ki} - M_i)/D_i$, where $e_{ki}$ represents the element of row k, column i in matrix A. Once A has been auto scaled, an extraction of principal components is carried out. The principal component extraction process is a standard technique not described here. The principal components are made up of a linear combination of the columns of the auto scaled matrix A.

The result of the extraction of principal components carried out on a set of measurements with patterns or calibrated gases is a diagram 25 of arbitrary units in which those measurements are situated. The last step in the learning process consists in defining decision boundaries between the zones of pure carbon dioxide, contaminated carbon dioxide at alert level and contaminated carbon dioxide at alarm level.

Figure 3:
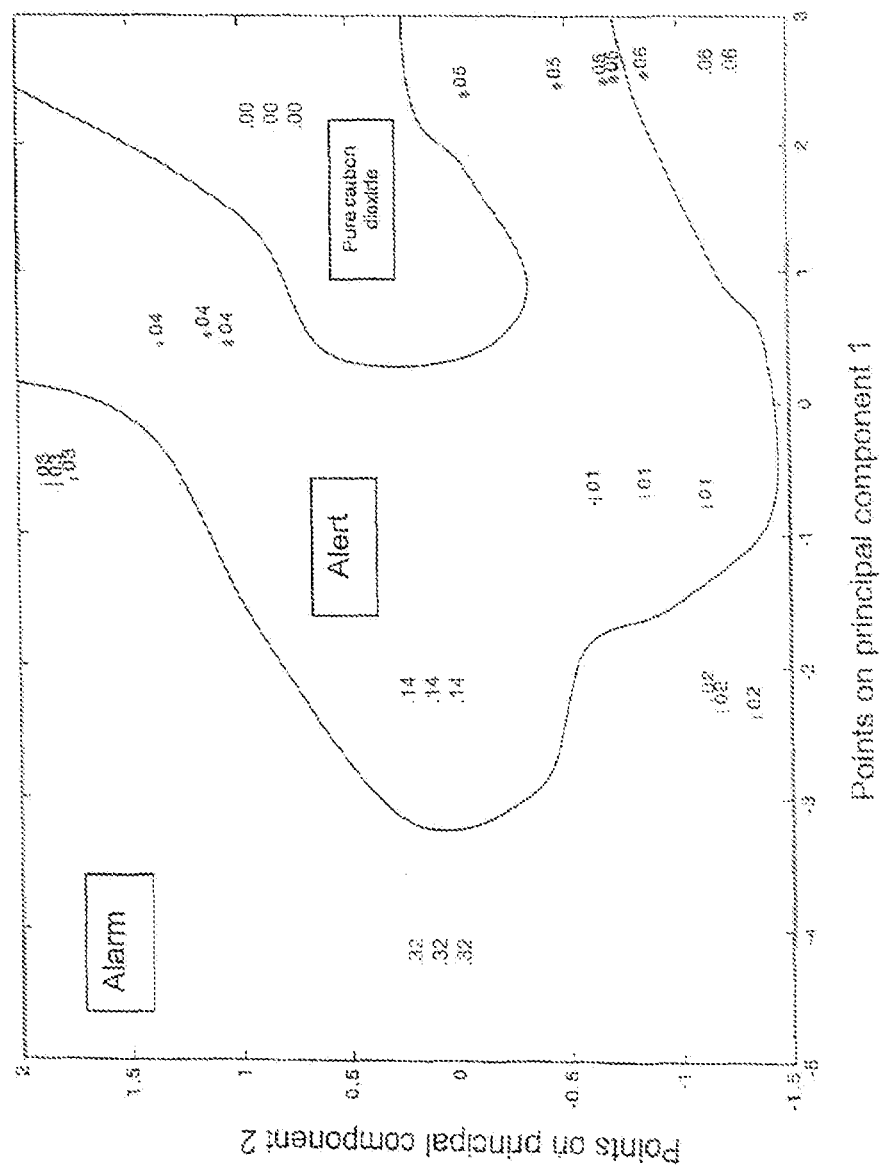
FIG. 3 shows a diagram or space of the principal components with zones or areas of decision delimited for pure carbon dioxide, carbon dioxide at alert level and carbon dioxide at alarm level.

FIG. 3 shows a diagram 25 with decision zones or areas delimited for pure carbon dioxide, contaminated carbon dioxide at alert level and contaminated carbon dioxide at alarm level. Said diagram 25 was obtained with the learning process by using the measurements with the calibrated gases or patterns 26. Reference 00 relates to a measurement with pure carbon dioxide, while references 01, 02, 03, 04, 05, 06, 14 and 32 relate to measurements of carbon dioxide with different types or mixtures of contaminants.

In FIG. 3:
00: pure CO2
01: CO2+10 ppm ethylene
02: CO2+20 ppm ethylene
03: CO2+30 ppm methane
04: CO2+15 ppm methane
05: CO2+0.5 ppm sulfur dioxide
06: CO2+1 ppm sulfur dioxide
14: CO2+10 ppm ethylene+15 ppm methane
32: CO2+20 ppm ethylene+30 ppm methane In said diagram 25, it can be observed that the pure carbon dioxide is clearly differentiated from the contaminated carbon dioxide. Different types of contamination are also observable, since the measurements of a single type, for example pure carbon dioxide, appear grouped in the space of the first two principal components, while the measurements of carbon dioxide affected by different contaminants occupy different positions in the space from the first two principal components.

The data recognition system 24 described identifies the measurements taken in the carrier gas 21, in this case carbon dioxide, according to the algorithm: a) Obtaining of a new conductance-variation vector or new measurement that has to be identified. b) Auto scaling of the vector, using the means and variances used to auto scale the learning matrix A. c) Projection of the auto scaled vector on the space of the principal components. d) Depending on the position occupied by said vector, the system decides which type of outlet has been identified.

Figure 4:
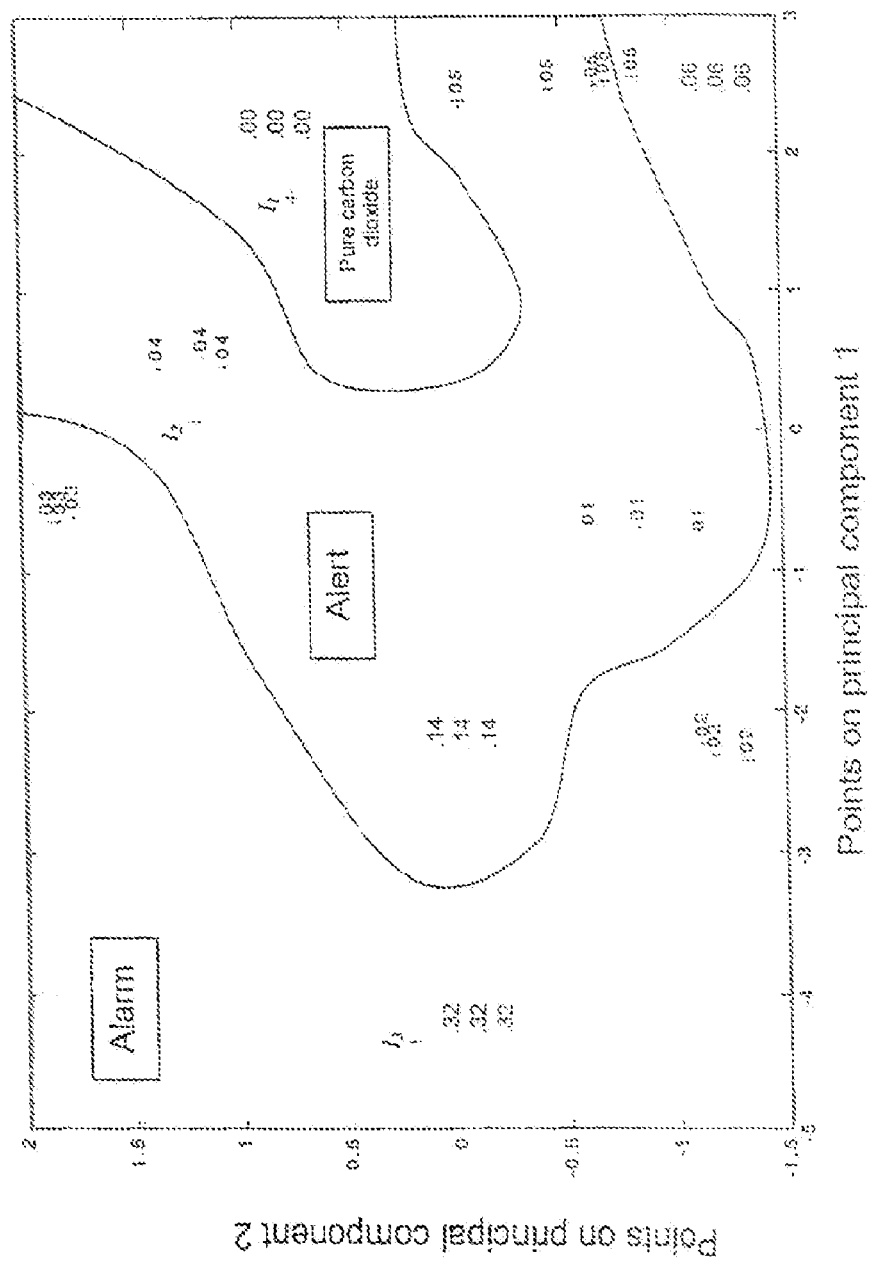
FIG. 4 shows a diagram or space of the principal components on which three measurements taken on the carbon dioxide have been projected, corresponding to the three vectors $I_1$, $I_2$ and $I_3$.

FIG. 4 shows a diagram or space 25 of the principal components onto which three measurements have been projected, corresponding to the three vectors $I_1$, $I_2$ and $I_3$. These measurements must be identified by the recognition system 24. Given the position occupied by projection $I_1$, it is concluded that said measurement pertains to pure carbon dioxide. The position of $I_2$ is very close to that of the calibration measurements with methane, so it is concluded that this measurement corresponds to an alert level due to methane contamination in the carbon dioxide. The position of $I_3$ is very close to that of the calibration measurements with methane and ethylene, so it is concluded that this measurement corresponds to an alarm level due to methane and ethylene contamination in the carbon dioxide.

The gas sensors 23 suffer from temporary deviations in their response. These deviations can be associated with raw material ageing processes. Therefore, in order to maintain the analyzing system in good operational order over time calibrations have to be carried out periodically. The system implements these calibrations in an automated way transparent to the user/operator. At preset intervals, such as every twenty-four hours, the system enters self-calibration mode. In this mode the following steps are carried out: a) Taking a measurement with each of the calibrated patterns: pure carbon dioxide, carbon dioxide with contaminant alarm level 1, carbon dioxide with contaminant alarm level p, where p is the number of contaminants detected in the carbon dioxide. b) Auto scaling and projection of the calibration measurements onto the space 25 of the principal components. c) Reckoning of the distances of each of the calibration measurements from the centroid of the class to which they belong. If that distance exceeds a certain preset measurement, new decision boundaries are recalculated taking account of the information provided by the calibration measurements.

Once the self-calibration process has ended, the equipment is ready to proceed with the real-time analysis of the quality of the carbon dioxide or carrier gas.

Although one specific embodiment of the invention has been described and shown, it will be clear that an expert on the subject could introduce variations and modifications, or replace the details with others that are technically equivalent, without departing from the sphere defined by the attached claims.

What is claimed is:

1. An analyzing system for the detection of reducing and oxidizing gases in a carbon dioxide gas flow whose quality is to be evaluated, said carbon dioxide gas having an oxygen content not exceeding 30 ppm of oxygen, which comprises:
    a plurality of detecting means, wherein said detecting means are chemiresistor gas sensors each of them comprising a semiconductor-type metal-oxide active layer, metallic electrodes to monitor the changes in the electrical conductivity of the semiconductor layer and heating means,
    a sealed measuring chamber into which said plurality of gas sensors are located,
    means for connecting said carbon dioxide gas flow to said measuring chamber so that a carbon dioxide gas flow is supplied through said chamber, the measurements being performed inside said chamber while said sensors are exposed to said carbon dioxide gas flow,
    wherein the sensing mechanism of the system involves the monitoring of conductivity changes of each sensor which take place in response to the presence of said pollutant gases contained in the carbon dioxide gas flow, and take place without the need to introduce additional oxygen into the sensor's structures during measurement,
    wherein the system further comprises calibrating means including pure carbon dioxide gas and contaminated carbon dioxide gas, and
    means for processing and control of acquisition and data recognition including a system of real-time recognition of said pollutant gases, which provides a diagram with delimited decision zones for pure carbon dioxide gas and contaminated carbon dioxide gas, in which the measurements taken on the carbon dioxide gas are situated and identified.

2. An analyzing system according to claim 1, wherein said calibration means include a plurality of patterns or calibrated gases at least equal in number to the number of reducing and oxidizing gases that have to be detected in the carbon dioxide gas flow, wherein the response of the plurality of sensors to the measurements of patterns includes the obtaining of a vector of conductance variation for each calibrated gas or standard.

3. An analyzing system according to claim 2, wherein said recognition means comprises obtaining a learning matrix resulting from grouping the conductance variation vectors of the measurements taken with the plurality of patterns or calibrated gases.

4. An analyzing system according to claim 3, wherein said recognition means identifies the measurements taken in the carbon dioxide gas flow, according to the algorithm:
    obtaining a vector of conductance variation for the plurality of sensors;
    auto scaling of the vector with mean values and variances used to auto scale a learning matrix obtained from the patterns or calibrated gases;
    projecting the auto scaled vector onto a space of the principal components extracted on the basis of the learning matrix obtained with the calibration means; and
    identifying a type of response, dependent upon the position occupied by the vector.

5. An analyzing system according to claim 4, wherein the type of response identified by the recognition means includes the responses of pure carbon dioxide, contaminated carbon dioxide at alert level due to at least one contaminant and contaminated carbon dioxide at alarm level due to at least one contaminant.

6. An analyzing system according to claim 1, wherein said processing and control means include a microprocessor that corrects temporary deviations of the sensor responses and controls and processes the data that permit detection of the presence of reducing and/or oxidizing gases at various pre-established levels.

7. An analyzing system according to claim 1, wherein said connecting means comprise a plurality of electrically operated valves and connecting pipes to permit the carbon dioxide gas or calibrated gases to flow through the chamber that contains the sensors.

8. An analyzing system according to claim 1, wherein utilization of the gas sensor based on semiconductor-type metal oxides is proposed for detecting reducing and oxidizing gases present in a carbon dioxide gas flow having an oxygen content not exceeding 30 ppm of oxygen.

9. An analyzing system according to claim 1, for the detection of reducing and oxidizing gases (pollutant gases) selected from the group consisting of propane, butane, hexane, methane, ethylene and sulfur dioxide.

10. A system for detecting reducing and oxidizing gases in a carbon dioxide gas flow whose quality is to be evaluated, said carbon dioxide gas having an oxygen content not exceeding 30 ppm of oxygen, which system comprises:
    a plurality of chemiresistor sensors each of which sensors comprises a semiconductor-type metal-oxide active layer, metallic electrodes to monitor the changes in the electrical conductivity of the semiconductor layer, and heating means,
    a scaled measuring chamber into which said plurality of gas sensors are located,
    calibration means comprising a plurality of patterns or calibrated gases at least equal in number to the number of reducing and oxidizing gases that have been detected in the carbon dioxide; and
    means for processing and control of acquisition and data recognition, wherein the sensing mechanism of the system involves the monitoring of the conductivity changes of each sensor which take place in response to the presence of pollutant gases contained in said carbon dioxide gas flow, and which take place without the need to introduce additional oxygen into the sensor's structures during measurement, wherein said means of processing and control include a system of real-time recognition of said gases, which provides a diagram with delimited decision zones, in which the measurements taken on said carbon dioxide gas are situated and identified, wherein the response of the plurality of sensors to the measurements of patterns includes obtaining a vector of conductance variation for each calibrated gas or standard, and wherein said recognition system comprises obtaining a learning matrix resulting from grouping the conductance variation vectors of the measurements taken with the plurality of patterns or calibrated gases.

11. An analyzing system according to claim 10, wherein said recognition system identifies the measurements taken in the carbon dioxide gas, according to the algorithm:

obtaining a vector of conductance variation for the plurality of sensors;

auto scaling of the vector with mean values and variances used to auto scale a learning matrix obtained from the patterns or calibrated gases;

projecting the auto scaled vector onto a space of the principal components extracted on the basis of the learning matrix obtained with the calibration means; and identifying a type of response, dependent upon the position occupied by the vector.

12. An analyzing system according to claim 11, wherein the type of response identified by the system includes the responses of pure carbon dioxide gas, contaminated carbon dioxide gas at alert level due to at least one contaminant and contaminated carbon dioxide gas at alarm level due to at least one contaminant.

13. An analyzing system according to claim 10, wherein said processing and control means include a microprocessor that corrects temporary deviations of the sensor responses and controls and processes the data that permit detection of the presence of reducing and/or oxidizing gases at various pre-established levels.

* * * * *